United States Patent [19]

Markowitz et al.

[11] Patent Number: 4,505,276
[45] Date of Patent: Mar. 19, 1985

[54] DEVICE FOR DETECTING RETROGRADE CONDUCTION

[75] Inventors: Harold T. Markowitz, Ham Lake; John C. Rueter, Shoreview; Edwin G. Duffin, New Brighton, all of Minn.

[73] Assignee: Medtronic, Inc., Minneapolis, Minn.

[21] Appl. No.: 504,707

[22] Filed: Jun. 15, 1983

[51] Int. Cl.³ ............................................. A61B 5/04
[52] U.S. Cl. .................................. 128/697; 128/419 P
[58] Field of Search ............. 128/419 PT, 419 P, 697, 128/702, 703, 710, 711

[56] References Cited

U.S. PATENT DOCUMENTS

| | | | |
|---|---|---|---|
| 3,593,705 | 7/1971 | Thomas et al. | 128/703 |
| 3,606,882 | 9/1971 | Abe et al. | 128/703 |
| 3,809,071 | 5/1974 | Davolos et al. | 128/702 |
| 3,832,994 | 9/1974 | Bicher et al. | 128/702 |
| 3,903,897 | 9/1975 | Loollons et al. | 128/419 P |
| 3,908,641 | 9/1975 | Judson et al. | 128/710 |

OTHER PUBLICATIONS

Celler et al., "Medical and Biological Engineering" vol. 14, No. 5, Sep. 1976, pp. 501–508.

Primary Examiner—William E. Kamm
Attorney, Agent, or Firm—Glenn W. Bowen; John L. Rooney; Joseph F. Breimayer

[57] ABSTRACT

A pacing system analyzer is constructed to provide verification that an implantable cardiac pacer operating in a demand mode will not itself produce tachycardia in a patient because of abnormally long patient retrograde conduction time. The analyzer when performing the retrograde conduction test provides an intercardiac electrogram, changes the ventricular sense amplifier to asynchronous and samples to determine the maximum amplitude signals over a sampling period to select an amplifier gain factor. After the gain factor is set additional signal samples are collected, peak-to-peak amplitude is measured and interpolation between data is made to provide waveform "segments" and the best waveform segment to employ for testing for retrograde conduction is selected. The time periods from pacing to these segments are measured and utilized to determine if retrograde conduction is present.

9 Claims, 5 Drawing Figures

DEVICE FOR DETECTING RETROGRADE CONDUCTION

BACKGROUND OF THE INVENTION

The present invention is related to cardiac pacing system analyzers which are designed to test the electrical performance of implantable cardiac pulse generators and the associated pacing lead system at the time of pacemaker implantation and during invasive pacemaker trouble-shooting or evaluation procedures. In particular, the present invention is related to a device and method for testing for retrograde conduction in patients to determine if certain types of cardiac pacemakers are contraindicated.

The normal heart controls pumping of the heart through a conduction system which provides electrical stimulating pulses at a rate that is appropriate for the body's needs. The sino-atrial (SA) node is a small knot of cells which is buried in the roof of the right atrium. It is at this point that the contraction of the heart is initiated, and the SA node is, therefore, called the pacemaker of the heart. Lower in the rear wall of the right atrium, and towards the midline of the heart, there is another knot of cells called the atrio-ventricular (A-V) node. The A-V node is connected to a bundle of long cell fibers which pass down and separate the two ventricles. This bundle of fibers is called the Bundle of His.

The Bundle of His splits into two bundle branches called Purkinje fibers. The cells of the SA node have a property of being able to exclude sodium for a period of time when the cells are "polarized." However, there is a constant low leakage of sodium into the cell and gradually the membrane of the cell reaches a point where the membrane potential causes it to "break down" and a rush of sodium into the cell takes place. This rush of sodium into the cell is called depolarization which results in an electrical discharge which causes a wave-like disturbance to spread from the SA node, causing depolarization of the atrial muscles of the heart. The atria then contract to empty blood into ventricles.

There is, however, no direct transmission of the depolarization wave from the atrial muscle to the ventricular muscle. Conduction into the ventricles occurs after firing of the A-V node as a result of the depolarization wave which spreads to the atria. When the atria are empty, and ventricular filling is completed, the A-V node fires, and the impulse is conducted out of the A-V node down through the Bundle of His and into the Purkinje system. This conduction into the ventricle portion of the heart causes all portions of the ventricular myocardium to contract almost simultaneously, which results in a very effective forceful contraction of pumping action.

Because of the unique construction of the cells of the heart and the construction of the conduction system of the heart, it is possible for an impulse to be conducted backward up through the conduction system, as well as forward in the normal fashion. Any reverse conduction through the heart conduction system is called a "retrograde conduction". Although the SA node in a normal heart controls the origin of the pacing synchronization pulses, cardiac cells have the capability of undergoing spontaneous depolarization and, thereby, establishing other sites as pacemaking sites. This will occur, for example, when the SA node is not operating in the proper manner, and a pacing site in a ventricle chamber takes over as the control site, so that there is an ectopic ventricular focus which causes conduction in the reverse manner through the His/Purkinje system.

The A-V junction may also provide an A-V junctional focus which causes retrograde activation of the atria. It is also possible for an artificial cardiac pacemaker to induce depolarization of the ventricle in a fashion such that reverse conduction or retrograde conduction may occur if the heart is not in heart block.

In other words, if the conduction channel of the His/Purkinje system is operative, a retrograde impulse can initiate atrial contractions which may result in the implanted cardiac pacemaker inducing tachycardias at the upper pacing rate limit of the artificial pacemaker when the patient has a dual chamber pacemaker with an atrial refractory time that is shorter than the patient's retrograde conduction time. Since the dual chamber pacemaker is becoming increasingly favored among cardiologists because of its improved physiologic properties which allows the patient to lead a more normal life, the problem of detecting the potential that such a pacemaker may have for inducing tachycardia of this type is a major consideration of the cardiac pacemaker field.

In a pacemaker in which there is atrial pacing, it is possible for the patient's retrograde conduction time to be longer than the atrial refractory time of the pacemaker. The atrial refractory time is the time that the atrial sense amplifier is deactivated and, therefore, is not capable of sensing pulses which are interpreted by the pacemaker as atrium, or P-wave, pulses. A short atrial refractory time of pacing of the ventricle chamber can cause a retrograde conducted depolarization wave to be sent by the atrial sense amplifier, which can cause the pacemaker to fire another ventricle pulse that will be sensed thereby eventually resulting in pacemaker induced tachycardia by forcing the pacemaker to go to its upper rate limit.

Modern dual chamber physiologic pacemakers are generally capable of operating either in the atrial synchronous, ventricular-inhibited (VDD) or the ventricular demand (VVI) modes. The present invention is useful when preliminary indications indicate demand pacing mode may be proper for the patient, but before implantation is complete, the physician wishes to ensure that the pacemaker will not itself produce tachycardia because of an abnormally long patient retrograde conduction time. The invention is also useful in universal, or DDD pacemakers which have provisions for intracardiac electrograms.

DESCRIPTION OF THE DRAWINGS

The present invention is described by reference to the drawings.

TECHNICAL DESCRIPTION OF THE INVENTION

Figure 1:
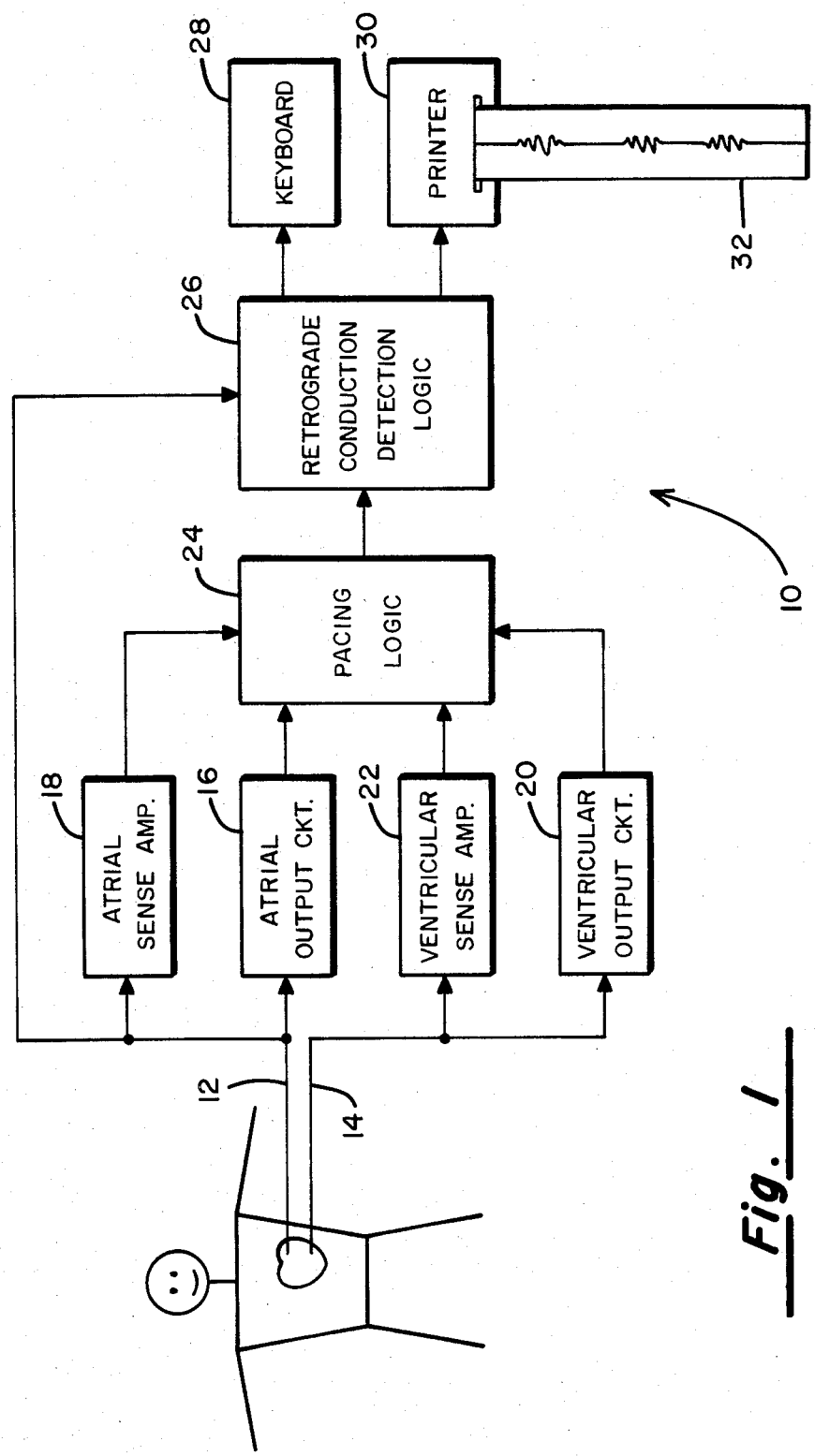
FIG. 1 is a block diagram, an implementation of the present invention.

FIG. 1 shows the block diagram implementation of the present invention in which the atrial lead 12 and the ventricular lead 14 are coupled to an atrial output circuit 16 and an atrial sense amplifier 18; and to ventricular output circuit 20 and a ventricular sense amplifier 22, respectively. These input and output circuits are coupled to the pacing control logic of a pacing system analyzer, which may be of a custom or of a conventional type. The pacing logic is coupled to the retrograde conduction logic 26 which is the subject of the present invention. The retrograde conduction logic is connected to a keyboard 28 for energizing and controlling the pacing system analyzer in response to the keyboard and a printer 30 for printing out the results of the retrograde conduction test on a printout strip 32.

Figure 2:
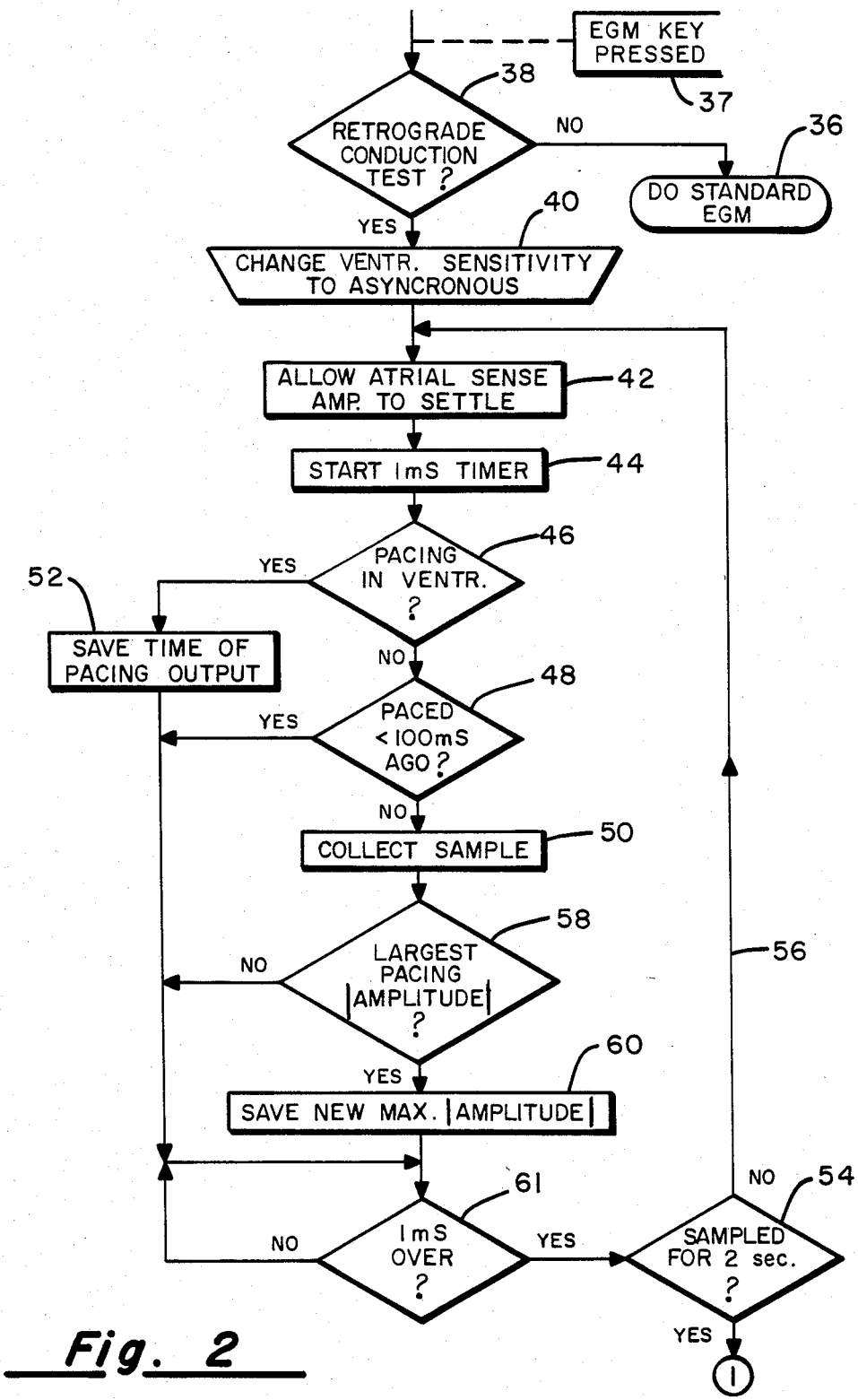
FIGS. 2–4 are flowchart representations of an implementation of the present invention in the pacing system analyzer.
Figure 3:
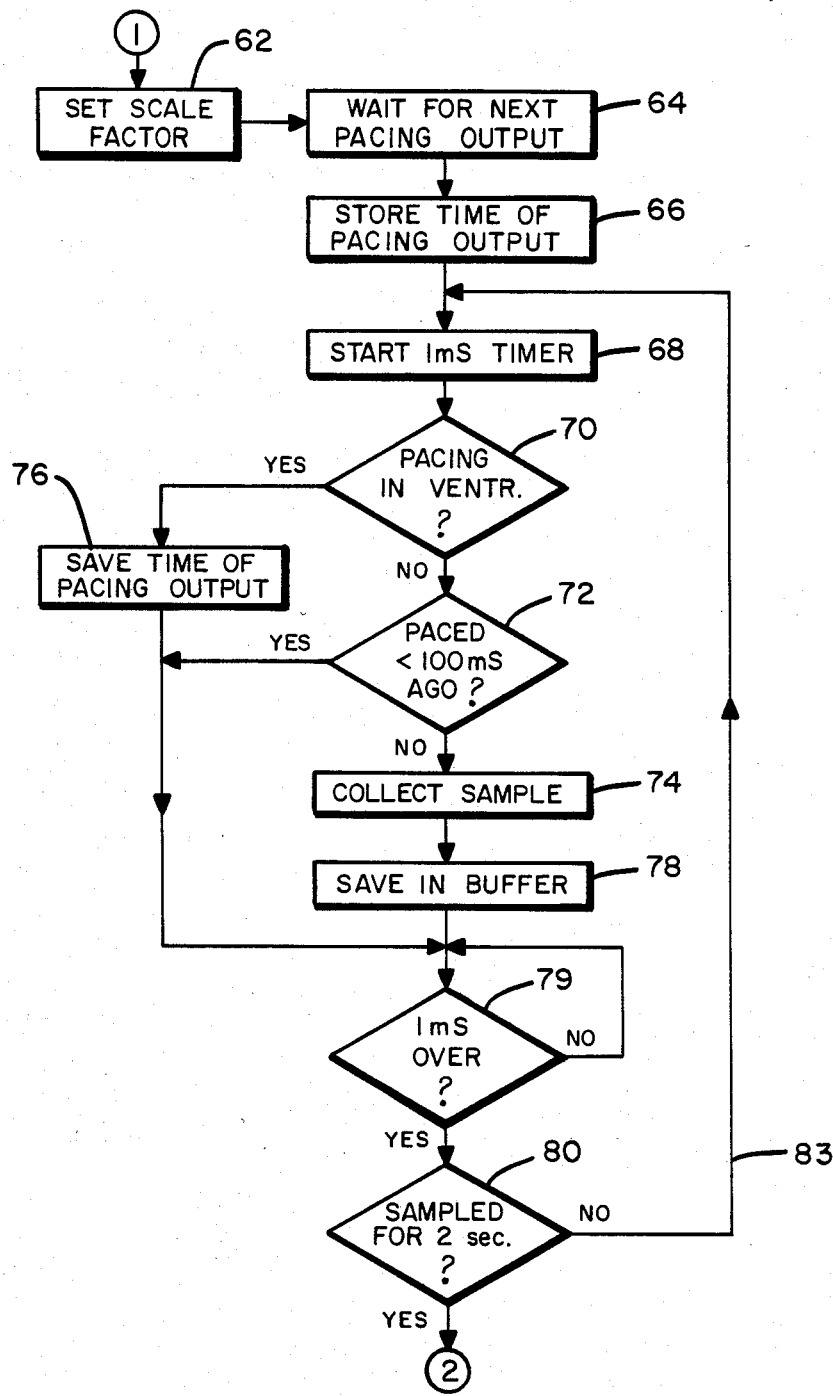
Figure 4:
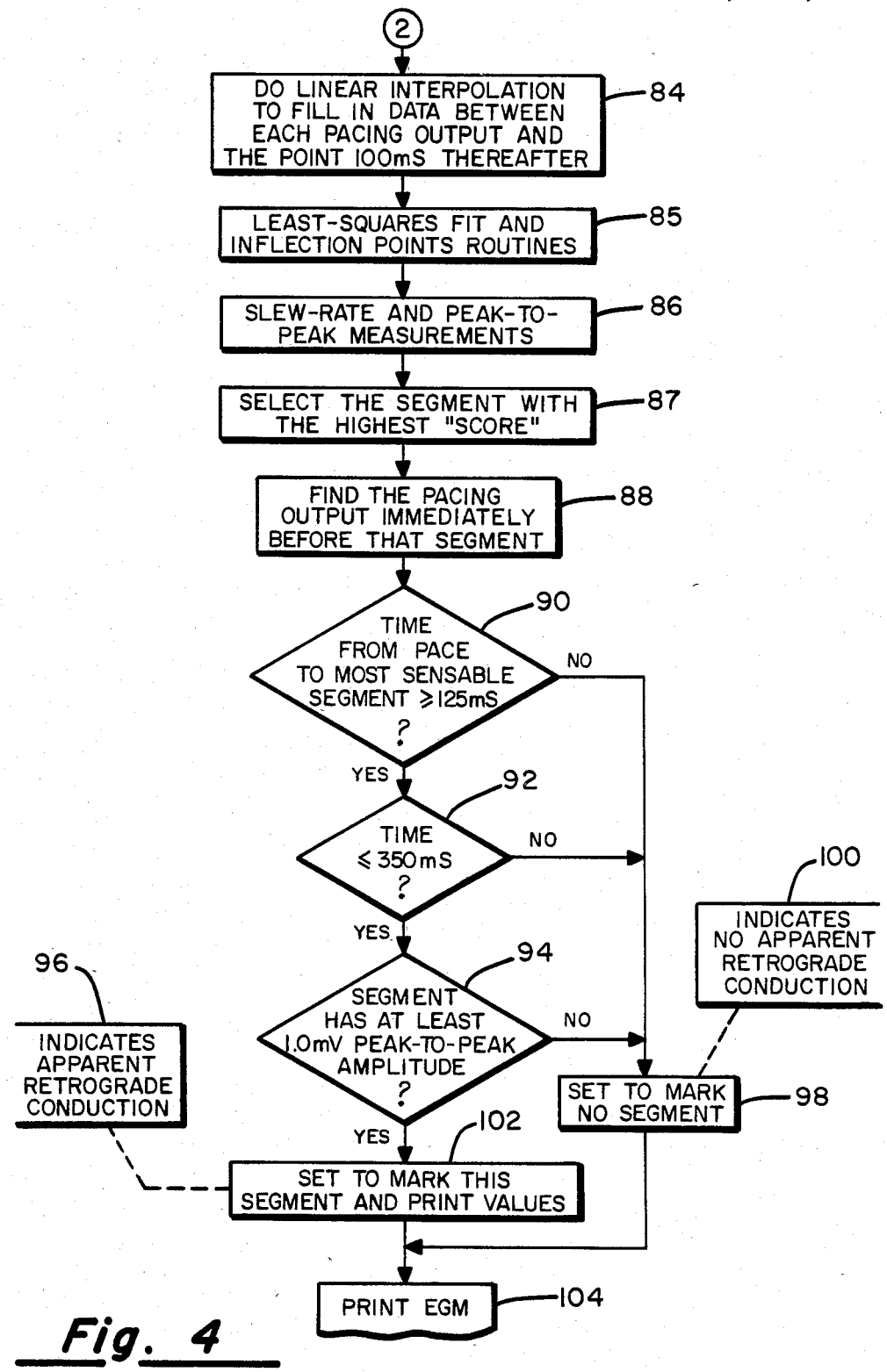

The implementation of the present invention through software control of a microprocessor in the implantable pacemaker is indicated by the flowcharts of FIGS. 2–4. It will be apparent to one skilled in the art, that the present invention may also be implemented with hardware. In FIG. 2, the comment 34 indicates that an electrocardiogram (EGM) is to be obtained from the atrial chamber. In order to obtain an atrial EGM from an artificial pacemaker, with the capability of sending one, the atrial lead must not be receiving pacing pulses. Therefore, the pacemaker will be switched to a VVI, or ventricular demand mode pacing at that time. In the event that an EGM is to be obtained, a test is performed, either by software or by a hardware implementation, to see if the retrograde conduction test key has been selected. If it has not, the operation step 36 indicates that a standard EGM will be obtained. If the decision of step 36 is "Yes" a retrograde conduction test is to be performed, and the action taken step 40 therefore, is to change the ventricular sensitivity to asynchronous. Ventricular pacing pulses are then supplied at the lower rate specified by the physician.

A summary of the retrograde conduction test feature which is activated by initiating an atrial EGM while the VVI pacing mode is in effect is as follows:

(1) The pacing system analyzer (PSA) paces asynchronously in the ventricles while the PSA samples the signal detected by the atrial lead system. The PSA takes two, 2-second signal samples as it does for a standard EGM printout.

(2) During atrial signal sampling, a 100 ms blanking interval initiated by each ventricular output pulse prevents the output pulse and the potentials occurring immediately following this event from affecting the automatic amplitude scaling and parameter measurement processes. This interval appears on the EGM as a straight line connecting the last data point before the start of the interval to the first data point following the interval.

(3) To facilitate interpretation and analysis, ventricular pacing stimuli, which do not appear because of the blanking interval, are marked on the EGM by simulated output pulses.

(4) Slew rate and peak-to-peak amplitude values will be printed on the EGM (with the measured waveform segment indicated) only if the "best scored" waveform segment falls within a window extending from 125 ms to 350 ms following each pacing stimulus and only if the waveform exceeds 1.0 mV in peak-to-peak amplitude.

The EGM printout preferably always begins with a ventricular output marker pulse.

Tests for retrograde conduction should be conducted prior to the implantation of a dual-chamber pacemaker with VDD or DDD pacing mode capabilities. In these modes, ventricular pacing stimuli are synchronized to sensed atrial activity. Retrograde conduction of paced ventricular activity that results in sensed atrial responses can result in a cyclic condition leading to pacing at the programmed rate setting. This condition occurs when the atrial response to retrograde conduction falls outside the atrial blanking or refractory period of the pulse generator. Thus, pacing modes that track atrial rate may be contraindicated in the presence of retrograde conduction.

Because multiple factors such as heart rate, drug treatments, or autonomic tone can influence retrograde conduction, negative EGM test results cannot be viewed as absolute indication of the absence of retrograde conduction. Such test results do not ensure that retrograde conduction will not occur or later develop following pacemaker implantation. Positive test results that document the presence of retrograde conduction should be carefully considered in the selection of the pulse generator to be implanted and/or the programmable pacing mode to be used.

Prior to conducting the following test procedure, obtain an unpaced atrial EGM to document intrinsic atrial waveforms. This EGM may be obtained as follows: (1) Select a desired pacing mode other than VVI and (2) Initiate an atrial EGM. This atrial EGM may be a helpful reference for comparison during the analysis of the test EGM.

The test for retrograde conduction should be conducted at 10 ppm intervals from just above the patient's intrinsic ventricular rate (or implantable pulse generator lower rate setting, whichever is greater) to the implantable pulse generator upper rate setting.

The test procedure includes the following steps:
(1) Select the VVI pacing mode and adjust pacing parameters for ventricular capture (use the pulse width and output voltage settings of the implantable pulse generator). Set pacing rate at the lower rate setting of the implantable pulse generator or 10 ppm above the patient's intrinsic ventricular rate, whichever is greater. The PSAF pulse width should not be set to less than 0.25 ms for this test procedure.

(2) Activate the EGM further so that ventricular pacing stimuli are delivered asynchronously at the selected rate for about 5 seconds during the EGM sampling period. Following this sampling period, VVI pacing returns and, after a few seconds of signal processing, the EGM printout begins. Allow the EGM to completely print out. The above procedure is then repeated at each 10 ppm rate increment up to the programmed upper rate setting of the implantable pulse generator.

A distinguishing characteristic of retrograde atrial responses is the consistent interval at which they occur following each ventricular stimulus marker pulse. This interval remains constant at any given ventricular pacing rate and typically falls within the range of 140 to 325 ms. If retrograde conduction is suspected, one or more additional test EGMs should be conducted at the same pacing rate to verify that the interval between the ventricular stimulus and the atrial response remains constant.

To facilitate test analysis, the PSA prints out on the EGM measured values of slew rate and peak-to-peak amplitude only when the "best scored" waveform segment falls within the "critical interval" window extending from 125 ms to 350 ms following each ventricular stimulus. As is discussed below, waveform segments within the 2-second sample period are automatically scored according to how easily they would be sensed by a typical implantable pulse generator based on the combination of slew rate and peak-to-peak amplitude. Significance of the critical window is that fast retrograde conduction occurring prior to 125 ms will fall within the atrial refractory or blanking period of the implantable pulse generator and will not affect its operation. Depending on the specific pulse generator, the refractory or blanking period may be greater than 125 ms. Beyond 350 ms, retrograde conduction is typically not seen.

Returning to the process steps, once the ventricular sensitivity is set to asynchronous, the atrial sense amplifier is allowed time to settle to avoid noise or false triggering noises, as indicated by step 42. At this point, the procedure conducts a two-second sampling mode in order to obtain a scale factor which is a function of the patient's own signal levels, and not of artifacts created within the analog hardware portion of the system. The pacing processor's ventricular pacing signal is also monitored during this time. During active periods of the ventricular pacing signals, and for 100 milliseconds thereafter, the artifact samples that are obtained are not used to provide an appropriate scale factor.

The scale factor determination is initiated by starting the 1 millisecond timer as indicated by the operational step 44. Once the timer is started, the samples that are obtained are used to make a decision, as indicated by decision step 46, as to whether or not there is pacing in the ventricular lead. If no pacing is occuring in the ventricular lead at this time, another decision is made at step 48, as to whether or not there was pacing less than 100 milliseconds ago.

If there was no pacing at this time, the operation step 50 allows for collection of the sample. If there was pacing, the control loops to operation step 52, which indicates the time that the pacing pulse issued. The test at decision step 54 then determines whether sampling has continued for two seconds. If the sampling has continued for two seconds, the scale factor is determined at step 62, where the gain factor is set in accordance with the samples obtained. The gain factor may be set by selection of one of a plurality of resistors coupled to an operational amplifier to control its gain in accordance with conventional resistor selection gain-control techniques.

A decision is then made, as indicated by the decision step 58, as to whether or not the particular sample that was collected has the largest pacing amplitude. If it does not, then the sampling decision of step 54 is again made on a later sample. However, if the sample that is collected is larger than the previous largest pacing amplitude, then the new magnitude of the maximum amplitude signal is saved as indicated by the operation step 60, before the decision is made as to whether sampling has continued for two seconds in the decision step 54.

Control returns to the decision step 46, in the event that there is pacing in the ventricle at the time the 1 millisecond timer is started. The time of this pacing pulse is stored, as indicated by the step 52, and finally a decision is made at step 54 if sampling has continued for two seconds and the 1 millisecond timer has timed out, as indicated by decision step 61. In the event the sampling has not continued for two seconds, the loop again follows line 56 back to the starting of the 1 millisecond timer Step 44.

Once the scale factor is set at step 62, based on the maximum amplitude determined during the two second sampling, the program waits for the next ventricular pacing output, as indicated by operational step 64. When this occurs, the time of the pacing output is stored as indicated by step 66. At step 68, the 1 millisecond timer is started again.

After the 1 millisecond timer has been started, steps 70, 72, 74 and 76 are followed which are similar to corresponding steps 46, 48, 50 and 52. At step 70 a decision is made as to whether or not there is pacing in the ventricular chamber. If there is no pacing, a decision is made at step 72 if there was pacing less than 100 milliseconds ago. If there was no pacing in this time frame, the step 74 indicates that a sample is to be collected. In the event that there was pacing is determined at either step 70 or step 72, the time of the pacing output is stored in the step 76, in a manner similar to the storage of step 52.

At step 78, the sample that is collected in this loop is stored in a buffer and here the procedure follows a different path than that previously followed after step 50. Following storage of the sample in the buffer, a decision is made at step 81 as to whether or not the 1 millisecond timer is timed out and if it is not, it loops back on itself until it times out. After the 1 millisecond timer has timed out a decision at the decision step 80 is made as to whether or not the sampling has occurred for a period of two seconds. If sampling has not occurred for two seconds a loop back on path 83 is followed to restart the 1 millisecond timer at step 68. If the sampling has continued for two seconds, the procedure steps to the interpolation step 84 of FIG. 4.

The waveform sampling that has occurred thus far, therefore, results in a series of digitized values that are stored in the memory which are representative of the waveform. At the step 84 in the process, a linear interpolation is performed to fill in between each pacing output data point and the data point 100 milliseconds later. Following this linear interpolation, the procedure then determines the "most sense-able" waveform, or line segment. The "most sense-able" waveform segment is one that has the best overall characteristic for being sensed by a pacemaker sense amplifier. That is, this is the first segment that would have been sensed by an amplifier that was being adjusted from a completely unsensitive state towards more and more sensitivity.

The manner in which the present invention achieves the detection of cardiac waveforms eliminates the necessity of using a "sensitivity" setting for pacing while making a measurement. It solves the problems of measuring slew-rate and peak-to-peak amplitude of waveforms in such a way as to include the entire waveform segment, including notches, where appropriate, in the same way that a pacemaker sense amplifier would. This technique, therefore, is useful for evaluating the position of an intercardiac pacing lead, for doing electrophysiologic studies and for detecting retrograde P-wave conduction.

Once the interpolation step 84 has been completed, the procedure for finding the "most sense-able" segment is initiated. The first step 85 of this procedure involves least-squares fit and inflection points of step 85. Least-squares fit and inflection point routines are commonly employed in data compression schemes and are well known to those skilled in the art. In the present application in these routines the slope of the line segment of 8 consecutive data points, may be found by examining the digital values that are stored. For example, values representative of the slope of a set of data points N through N+7 may be examined to see if this slope is different from the slope represented by another set of points, for example, N+1 through N+8, (i.e., the slopes are not both positive, negative or substantially flat).

At each of the inflection points, the data points in the vicinity of this point are examined to find the left and right boundaries of the line which contain this slope. Desirably, notches and "flat" spots in the data are examined and accounted for also, in accordance with known data compression and waveform analysis techniques. When the end points of a line segment is determined, the slew rate and peak-to-peak measurements of the line segment are made in step 86. In step 87 these line segments are given a "score" and the segment with the highest "score" is selected as a "most sense-able" segment.

Figure 5:
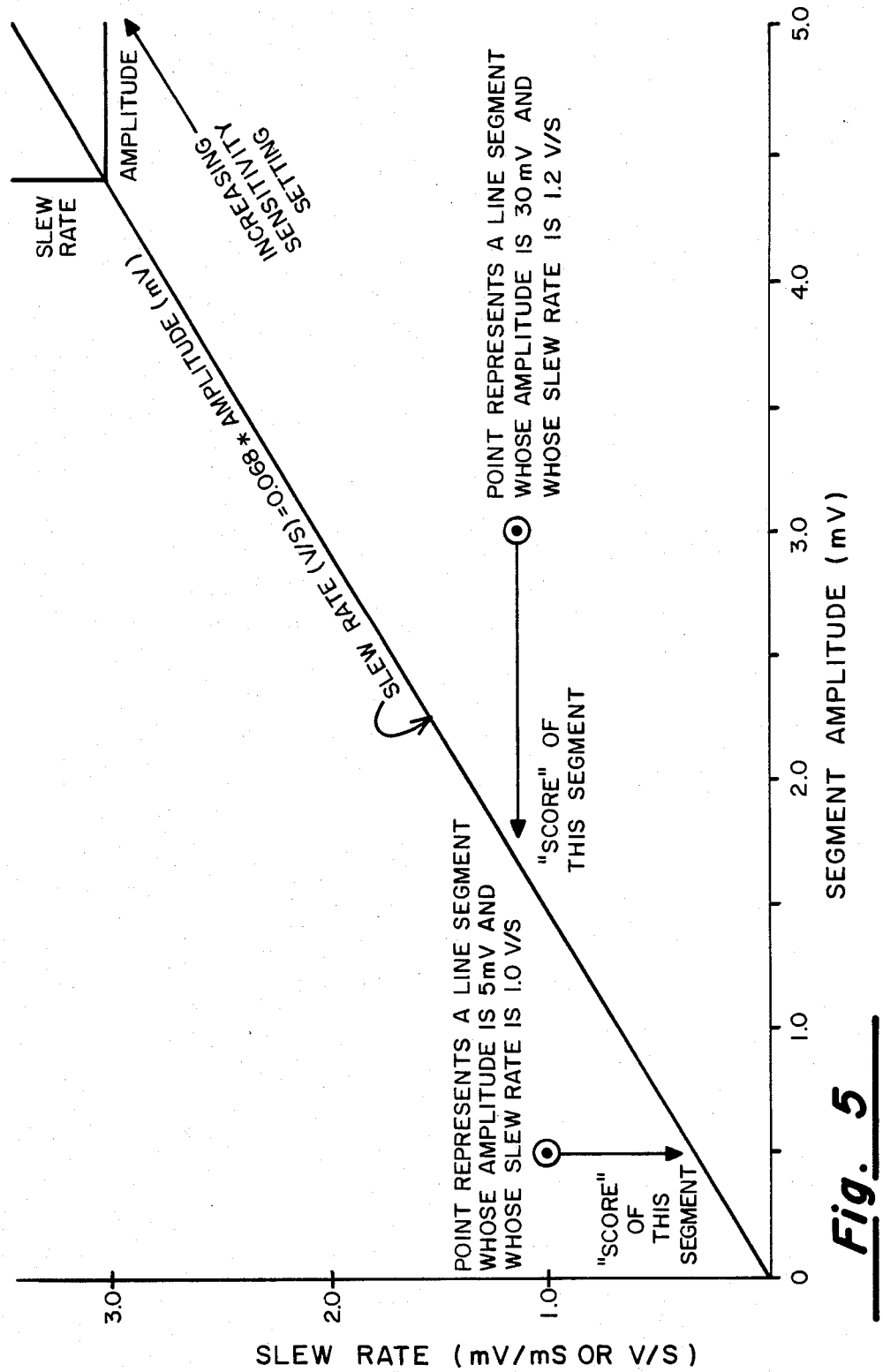
FIG. 5 is a graph that illustrates how the best waveform segment for sensing is determined.

The manner in which the segment with the highest "score" is selected is best understood by reference to FIG. 5. The advantage of proceeding in this manner is that the P-wave portion of the waveform can be determined despite the gain setting of the sense amplifier. This is because an analysis of commonly employed sense amplifiers in pacemakers show that there is a recurring relationship of slew rates (in volts/seconds) which is equal to approximately 0.068 times the amplitude (in millivolts). Therefore, adjusting a sense amplifier's sensitivity setting amounts to moving the perpendicular axis along a line whose slope is 0.068, with respect to the units defined in the graph of FIG. 5. A point on the line of this graph which is farther away from the origin than another point is "more sense-able" than a point that is closer to the origin. Thus points can be "scored" by determining the point on this line where a pair of coordinates representative of a line segment cross the line.

For points that are above the 0.068 line, this score is found by drawing a vertical line down through the sloping line. Thus the point which is representative of a line segment with an amplitude of 5 millivolts and a slew rate of 1.0 volts per second in FIG. 5 represents a segment that has more of a slew rate influence than an amplitude influence. The tip of the arrowhead on the vertical line from this point at the cross-over point of the sloping line indicates a score representative of this segment.

For points that are below the 0.068 line and to the right of the line, as, for example, the point which is representative of a line segment whose amplitude is 30 millivolts and whose slew rate is 1.2 volts per second is a point representative of a segment that has more of an amplitude influence than a slew rate influence. A score of this segment is determined by drawing a horizontal line to the cross-over point at the arrowhead at the end of this horizontal line.

From the above description it is seen that the point where the line segment whose amplitude is 30 millivolts and whose slew rate is 1.2 volts per second has a higher score than a point whose amplitude is 5 millivolts and a slew rate of 1.0 volts per second. The 30 millivolt amplitude line segment, therefore, would be "more sense-able" than the 5 millivolt line segment. As each line segment score is determined, this score is compared with the maximum score that has been found thus far and the best score is utilized and stored. A storage buffer may be employed for this process which is updated so that the lowest score stored in the buffer is always replaced with a higher score, and the process is repeated until the capacity of the buffer is reached.

The described procedure is effective in finding the waveform segments which are most easily detected by the sense amplifier and therefore, which can be more easily evaluated to determine if there is P-wave generation due to retrograde conduction. It is noted from the graph of FIG. 5 that any line segment must have a slew rate of at least equal to the cross-over point to be sensed. For example, if a line segment were generated which had an amplitude of 30 millivolts, but the slew rate was only 1.0 volts per second, it would not be sensed by the sense amplifier. In a similar manner a point which had a slew rate of 1.0 volts per second, but an amplitude of less than 5 millivolts would also not be sensed. Thus, it can be seen that the described routine is highly effective in determining the best waveforms that would be utilized for further processing.

Once a "most sense-able" line segment has been determined, the time of the pacing output immediately before that segment is determined at step 88. The program then proceeds to step 90 at which the time from the prior pacing output to a "most sense-able" segment is measured to determine whether or not this time is equal to or greater than 125 milliseconds. In the event that the time from the pacing to the "most sense-able" segment is not equal to or greater than 125 milliseconds, the program proceeds to step 98, which indicates that no segment on the printed-out tape is to be marked, as indicated by the comment 100. This is representative of the fact that there is no apparent retrograde conduction.

However, if the time measured in step 90 is equal to or greater than 125 milliseconds, then a second measurement is made and a second decision is determined at step 92 as to whether this time is equal to less than 350 milliseconds. Again, if the time determined in this step is not equal to or less than 350 milliseconds, the program goes to step 98 so that no segment of the output tape will be marked. However, if the time from pacing to the "most sense-able" segment was equal to or greater than 125 milliseconds, as determined by step 90, and was also equal to or less than 350 milliseconds, as determined by step 92, then a decision will be made at step 94, determining if this segment had at least a 1.0 millivolt peak-to-peak amplitude. If this peak-to-peak amplitude has not been obtained, again, the path is through step 98 and no segment is marked. However, if the condition of step 94 is satisfied so that a 1.0 millivolt peak-to-peak amplitude is reached, the printed-out tape is marked at this segment in step 102. As indicated by a comment indicator 96 this indicates that there is an apparent retrograde conduction, and when the EGM is printed out in step 104 the appropriate location will be marked as a result of step 102 so that the physician may be alerted to the necessity of further analysis to determine if retrograde conduction is present.

What is claimed is:

1. A device for detecting retrograde conduction of a heart comprising:
    atrial sense means for sensing atrial chamber signals during a sampling period while the ventricular chamber is being artificially asynchronously paced with pacing pulses,
    means for recording an electrogram representative of said atrial chamber signals,
    means for determining when a P-wave may have been sensed within a predetermined time window after each pacing pulse and,
    means for marking said electrogram at locations of possible P-waves.

2. A device as claimed in claim 1 further comprising means for scoring the slew rate and the amplitude of segments between sensed atrial signal data parts relative to the sensing characteristic of said atrial sense means to select only certain segments to be evaluated by said means for determining when P-waves may have been sensed.

3. A device as claimed in claim 2 further comprising means for measuring the peak-to-peak amplitude of possible P-waves within said time window and for indicating a possible P-wave only if a threshold value is exceeded.

4. A device as claimed in claim 3 further comprising means for scoring the slew rate and the amplitude of segments betweeen sensed atrial signal data parts relative to the sensing characteristic of said atrial sense means to select only certain segments to be evaluated by said means for determining when P-waves may have been sensed.

5. A device as claimed in claim 1 further comprising means responsive to said atrial sense means for setting the gain of said atrial sense means during a sampling period which precedes the sampling period which supplies the signals that are evaluated to determine possible P-waves.

6. A device as claimed in claim 5 further comprising means for scoring the slew rate and the amplitude of segments between sensed atrial signal data points relative to the sensing characteristic of said atrial sense means to select only certain segments to be evaluated by said means for determining when P-waves may have been sensed.

7. A device as claimed in claim 6 further comprising means for measuring the peak-to-peak amplitude of possible P-waves within said time window and for indicating a possible P-wave only if a threshold value is exceeded.

8. A device as claimed in claim 7 wherein said time window is approximately 225 milliseconds wide and starts approximately 125 milliseconds after each pacing pulse.

9. A device as claimed in claim 8 when said peak-to-peak amplitude is approximately 1.0 millivolts.

* * * * *